US007662619B2

(12) United States Patent
Kingsley et al.

(10) Patent No.: US 7,662,619 B2
(45) Date of Patent: Feb. 16, 2010

(54) SOL-FUSIN: USE OF GP64-6HIS TO CATALYZE MEMBRANE FUSION

(75) Inventors: David H. Kingsley, Magnolia, DE (US); Joshua Zimmerberg, Bethesda, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 1000 days.

(21) Appl. No.: 10/416,979

(22) PCT Filed: Nov. 15, 2001

(86) PCT No.: PCT/US01/44909

§ 371 (c)(1),
(2), (4) Date: Oct. 3, 2003

(87) PCT Pub. No.: WO02/40504

PCT Pub. Date: May 23, 2002

(65) Prior Publication Data
US 2004/0052819 A1      Mar. 18, 2004

Related U.S. Application Data

(60) Provisional application No. 60/249,415, filed on Nov. 15, 2000.

(51) Int. Cl.
C12N 15/00 (2006.01)
A61K 31/70 (2006.01)
(52) U.S. Cl. ...................................... 435/320.1; 514/44
(58) Field of Classification Search ................. 536/23.4; 514/2–21, 44; 530/350; 435/320.1
See application file for complete search history.

(56) References Cited

U.S. PATENT DOCUMENTS 5,919,480 A * 7/1999 Kedar et al. ................. 424/450
6,001,806 A 12/1999 Murphy et al.
6,261,554 B1 * 7/2001 Valerio et al. .............. 424/93.6

FOREIGN PATENT DOCUMENTS

WO    WO 9965465 A1 * 12/1999
WO    WO 00/64471        11/2000
WO    WO 01/93836        12/2001

OTHER PUBLICATIONS

Qiagen Product Guide, 1998; pp. 40-45.*
Mullins et al. (1996) J. Clin. Invest. vol. 98, pp. 1557-1560.*
Mullins et al. (1993) Hypertension vol. 22, pp. 630-633.*
Cameron (1997) Molec. Biotech. vol. 7, pp. 253-265.*
Kappel et al. (1992) Current Opinion in Biotechnology, vol. 3, pp. 548-553.*
Massotte et al. (Jour. Biotech. 1999, vol. 69, pp. 39-45).*
Lian et al. (J. Pharm. Sci. 2001, vol. 90, pp. 667-680).*
Miller et al. (FASEB J. 1995, vol. 9, pp. 190-199).*
Ambrosch. Immunogenicity and protectivity of a new liposomal hepatitis A vaccine. *Vaccine.* 15(11):1209-1213 (1997).
Gould-Fogerite et al. Chimerasome-mediated gene transfer in vitro and in vivo. *Gene.* 84:429-438 (1989).
Gregoriadis. Genetic vaccines: strategies for optimization. *Pharm Res.* 15(5):661-670 (1998).
Hollister. Stable expression of mammalian β1,4-galactosyltransferase extends tha N-glycosylation pathway in insect cells.. *Glycobiology.* 8(5):473-480 (1998).
Ishii et al. Cationic liposomes are a strong adjuvant for a DNA vaccine of human immunodeficiency virus type 1. *Aids Res. Hum. Retroviruses* 13(16):1421-1428 (1997).
Jarvis et al. Biosynthesis and Processing of the *Autographa californica* Nuclear Polyhedrosis Virus GP64 Protein. *Virology.* 205:300-313 (1994).
Kedar et al. Delivery of Cytokines by Liposomes. II. Interleukin-2 Encapsulated in Long-Circulating Sterically Stabilized Liposomes: Immunomodulatory and Anti-tumor Activity in Mice. *J Immunotherp.* 16:115-124 (1994).
Naruse. A potential peptide vaccine against two different strains of influenze virus isolated at intervals of about 10 years. *PNAS.* 91:9588-9592 (Sep. 1994).

(Continued)

*Primary Examiner*—J. E Angell
(74) *Attorney, Agent, or Firm*—Townsend and Townsend and Crew LLP

(57) ABSTRACT

The present invention provides an isolated nucleic acid comprising the nucleotides set forth in the Sequence Listing as SEQ ID NO: 1. SEQ ID NO: 1 is an example of GP64-6His nucleic acid. The invention further provides polypeptides encoded by GP64-6His nucleic acids as well as the polypeptide encoded by SEQ ID NO: 2. The invention also provides liposomes comprising GP64-6His polypeptides as well as liposomes comprising GP64-6His polypeptides and biological molecules. The invention further provides a method of increasing the solubility of polypeptides comprising linking a 6His tag to a polypeptide and measuring the solubility of the 6His-tagged polypeptide, whereby an increase in solubility of the 6His-tagged polypeptide can be detected. The invention also provides a method of solubilizing a viral fusion polypeptide comprising linking a 6His tag to a viral fusion polypeptide. Further provided is a method of delivering a biological molecule to a cell comprising, administering the liposome comprising a GP64-6His polypeptide to a cell. This invention also provides a method of delivering a viral vaccine to a cell comprising administering the liposome comprising a GP64-6His polypeptide to a cell. Also provided is a method of delivering a DNA vaccine to a cell comprising administering the liposome comprising a GP64-6His polypeptide to a cell. Further provided is a GP64-6His polypeptide further comprising a binding site for a cell surface molecule. Also provided by this invention are chimeric proteins comprising GP64-6His.

12 Claims, No Drawings

OTHER PUBLICATIONS

Okada. Intranasal Immunization of a DNA Vaccine with IL-12 and Granuloctye-Macrophage Colony-Stimulating Factor (GM-CSF)-Expressing Plasmids in Liposomes Induces Strong Mucosal and Cell-Mediated Immune Responses Against HIV-1 Antigens. *J. Immunol.* 159:3638-3647 (1997).

Vaage et al. Therapy of a xenografted human colonic carcinoma using cisplatin or doxorubicin encapsulated in long-circulating pegylated stealth liposomes. *Int J Cancer.* 80:134-137 (1999).

Vertut-Doi et al. Binding and uptake of liposomes containing a poly-(ethylene glycol) derivative of cholesterol (stealth liposomes) by the macrophage cell line J774: influence of PEG content and its molecular weight. *Biochim Biophys Acta.* 1278:19-28 (1996).

Working et al. Reduction of the Cardiotoxicity of Doxorubicin in Rabbits and Dogs by Encapsulation in Long-Circulating, Pegylated Liposomes. *J Pharmacol Exp Ther.* 289(2):1128-1133 (1999).

Kingsley et al., "A discrete stage of baculovirus GP64-medicated membrane fusion" Molecular Biology of the Cell 10(12):4191-4200 (1999).

Monsma et al., "Identification of a membrane fusion domain and an oligomerization domain in the baculovbirus GR64 envelope fusion protein" J. Virology 69(4):2583-2595 (1995).

Plonsky et al. "An Analysis of the Role of the Target Membrane on the GP64 induced fusion pore" Virology 253(1):65-76 (1999).

\* cited by examiner

SOL-FUSIN: USE OF GP64-6HIS TO CATALYZE MEMBRANE FUSION

This application claims the benefit of priority of U.S. Provisional Application No. 60/249,415, filed Nov. 15, 2000. The 60/249,415 provisional patent application is herein incorporated by this reference in its entirety.

BACKGROUND OF THE INVENTION

1. Field of the Invention

The present invention relates to the addition of histidine amino acids to the cytoplasmic domains of membrane and viral envelope proteins for the purposes of solubilizing, and/or reconstituting viral envelope proteins in lipid containing vesicles. The invention further relates to the use of GP64-6His to catalyze delivery of therapeutic, genetic, or antigenic compounds via fusion of lipid membranes or bilayers

2. Background Art

Enveloped viruses infect cells by one of two membrane fusogenic processes. The first is direct cell surface membrane fusion or pH-independent membrane fusion. Briefly, contact with the appropriate cell surface receptor activates viral envelope proteins to catalyze membrane fusion of the virus with the cytoplasmic membrane resulting in deposition of the infectious nucleocapsid inside the cell. A second class of enveloped viruses enters by receptor-mediated endocytosis or pH-dependent processes. pH dependent viruses also target their host cell by interaction with a specific receptor. However rather than fusing directly at the cell surface, these viruses remain attached to the receptor which is subsequently internalized within an endosomal vacuole derived from the cell surface lipids. This vacuole, termed an endosome, enters the lysosome. The lysosome is an acidic (low pH) cellular compartment which metabolizes, recycles, and breaks down endosomal contents. When pH-dependent enveloped viral proteins are exposed to the low pH of the lysosome, a conformational change occurs resulting in the activation of membrane fusion. These proteins then mediate fusion of the viral envelope with the lipid membrane to escape the lysosome. As a result, the virus is then free to replicate within the host cell.

Liposomes are small vesicles composed of phospholipid bilayers of varying compositions. As such they can be used to encapsulate, protect, and deliver therapeutic compounds, DNA, RNA (sense or antisense), or proteins to cells. Currently liposomal encapsulation systems have been of limited utility. There are two primary reasons for this: 1) While liposomes do in fact enter cells, they do so primarily by endocytosis. As discussed previously this process results in deposition of endosomal vacuoles within the lysosome. The acidic nature of the lysosome results in degradation or destruction of the liposomal contents, in most cases, 2) Liposomes, unlike viruses, lack the ability to discriminate between different cell and tissue targets, since they do not bind to specific receptors on the cell surface.

GP64 is a class I membrane glycoprotein, which constitutes the major envelope protein of the AcMNPV budded baculovirus virion (Volkman and Goldsmith, 1984; Volkman et al., 1984). This protein is both necessary and sufficient for mediating pH-dependent membrane fusion (Blissard and Wenz, 1992), and is essential for cell-cell transmission of the enveloped virion (Monsma et al., 1996).

When GP64 (or GP64-6His) is expressed on the cell surface of Sf9 insect cells, host and target cell membranes can be fused (syncytia formation) simply by application of acidic buffer solution (phosphate buffer saline or citrate buffer pH 5.5-4.8) This invention provides functionally competent GP64-6His protein to create acid-activated fusion competent liposomes for various biomedical and research purposes.

SUMMARY OF THE INVENTION

The present invention provides a GP64-6His nucleic acid. The present invention also provides an isolated nucleic acid comprising the nucleotides set forth in the Sequence Listing as SEQ ID NO: 1.

The invention further provides polypeptides encoded by GP64-6His nucleic acids. One example of such a polypeptide is the polypeptide encoded by SEQ ID NO: 2.

The invention also provides liposomes comprising GP64-6His polypeptides as well as liposomes comprising GP64-6His polypeptides and biological molecules.

The invention further provides a method of increasing the solubility of polypeptides comprising linking a 6His tag to a polypeptide.

Further provided is a method of delivering a biological molecule to a cell comprising: administering the liposome comprising a GP64-6His polypeptide to a cell whereby the GP64-6His mediates membrane fusion thus delivering the biological molecule to the cell.

This invention also provides a method of delivering a viral vaccine to a cell comprising: administering the liposome comprising a GP64-6His polypeptide and a viral fragment to a cell whereby the GP64-6His mediates membrane fusion thus delivering the viral vaccine to the cell.

Also provided is a method of delivering a DNA vaccine to a cell comprising: administering the liposome comprising a GP64-6His polypeptide and a DNA vaccine to a cell whereby the GP64-6His mediates membrane fusion thus delivering the DNA vaccine to the cell.

Further provided is a GP64-6His polypeptide further comprising a binding site for a cell surface molecule.

Also provided by this invention are chimeric polypeptides comprising GP64-6His.

DETAILED DESCRIPTION OF THE INVENTION

The present invention may be understood more readily by reference to the following detailed description of the preferred embodiments of the invention and the Example included herein.

Before the present compounds and methods are disclosed and described, it is to be understood that this invention is not limited to specific proteins, specific methods, or specific nucleic acids, as such may, of course, vary. It is also to be understood that the terminology used herein is for the purpose of describing particular embodiments only and is not intended to be limiting.

It must be noted that, as used in the specification and the appended claims, the singular forms “a,” “an,” and “the” include plural referents unless the context clearly dictates otherwise. Thus, for example, reference to “a nucleic acid” includes multiple copies of the nucleic acid and can also include more than one particular species of nucleic acid molecule.

The present invention provides an isolated nucleic acid comprising the nucleic acid set forth in the Sequence Listing as SEQ ID NO:1. This nucleic acid is an example of a GP64-6His nucleic acid.

As used herein, the term “nucleic acid” refers to single-or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for the GP-64 protein discussed herein or may include alternative codons which encode the same amino acid as that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides).

The nucleic acids provided for by the present invention may be obtained in any number of ways. One example of a method of obtaining a DNA molecule encoding a specific GP64-6His protein is to synthesize a recombinant DNA molecule which encodes the GP64-6His protein. For example, oligonucleotide synthesis procedures are routine in the art and oligonucleotides coding for a particular protein region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins can readily be synthesized by first constructing several different double-stranded molecules that code for particular regions of the protein, followed by ligating these DNA molecules together. For example, Cunningham, et al., "Receptor and Antibody Epitopes in Human Growth Hormone Identified by Homolog-Scanning Mutagenesis," Science, 243:1330-1336 (1989), have constructed a synthetic gene encoding the human growth hormone gene by first constructing overlapping and complementary synthetic oligonucleotides and ligating these fragments together. See also, Ferretti, et al., Proc. Nat. Acad. Sci. 82:599-603 (1986), wherein synthesis of a 1057 base pair synthetic bovine rhodopsin gene from synthetic oligonucleotides is disclosed. See also, U.S. Pat. No. 5,503,995 which describes an enzyme template reaction method of making synthetic genes. Techniques such as this are routine in the art and are well documented. By constructing a GP64-6His nucleic acid in this manner, one skilled in the art can readily obtain any particular GP64-6His protein with desired amino acids at any particular position or positions within the GP64-6His protein. These nucleic acids or fragments of a nucleic acid encoding a GP64-6His protein can then be expressed in vivo or in vitro as discussed below.

Once the nucleic acid sequence of the desired GP64-6His protein is obtained, the sequence encoding specific amino acids can be modified or changed at any particular amino acid position by techniques well known in the art. For example, PCR primers can be designed which span the amino acid position or positions and which can substitute any amino acid for another amino acid. Then a nucleic acid can be amplified and inserted into the wild-type GP64-6His protein coding sequence in order to obtain any of a number of possible combinations of amino acids at any position of the GP64-6His protein. Alternatively, one skilled in the art can introduce specific mutations at any point in a particular nucleic acid sequence through techniques for point mutagenesis. General methods are set forth in Smith, M "In vitro mutagenesis" Ann. Rev. Gen., 19:423-462 (1985) and Zoller, M. J. "New molecular biology methods for protein engineering" Curr. Opin. Struct. Biol., 1:605-610 (1991). These techniques can be used to alter the coding sequence without altering the amino acid sequence that is encoded.

The nucleic acids of this invention can also encode chimeric GP64-6His polypeptides. For the purposes of the invention, the term chimeric GP64-6His polypeptide is defined as including any polypeptide encoded by a nucleic acid where at least a portion of a nucleic acid encoding a GP64-6His polypeptide is coupled to at least a portion of a nucleic acid encoding another polypeptide. Protocols for construction of a vector containing a nucleic acid encoding the fusion protein of this invention are well known in the art (Sambrook et al., *Molecular Cloning: A Laboratory Manual.* 2nd Ed., Cold Spring Harbor Laboratory, Cold Spring Harbor, N.Y. (1989). For example, nucleic acid encoding a GP64-6His polypeptide or portion thereof of this invention can be ligated to a nucleic acid encoding another polypeptide according to standard molecular biology protocols such that a continuous open reading frame results which will allow for production of the chimeric protein. The nucleic acid encoding the chimeric protein can be placed into an expression vector, which can be obtained commercially or produced in the laboratory. These chimeric polypeptides can be any nucleic acid that functionally encodes the chimeric polypeptide. To functionally encode the polypeptide (i.e., allow the nucleic acid to be expressed), the nucleic acid can include, for example, expression control sequences, such as an origin of replication, a promoter, an enhancer and necessary information processing sites, such as ribosome binding sites, RNA splice sites, polyadenylation sites and transcriptional terminator sequences. Preferred expression control sequences are promoters derived from metallothionine genes, actin genes, immunoglobulin genes, CMV, SV40, adenovirus, bovine papilloma virus, etc. A nucleic acid encoding a selected chimeric polypeptide can readily be determined based upon the genetic code for the amino acid sequence of the selected chimeric polypeptide and many nucleic acids will encode any selected chimeric polypeptide. Modifications in the nucleic acid sequence encoding the chimeric polypeptide are also contemplated. Modifications that can be useful are modifications to the sequences controlling expression of the chimeric polypeptide to make production of the chimeric polypeptide inducible or repressible as controlled by the appropriate inducer or repressor. Such means are standard in the art. The nucleic acids can be generated by means standard in the art, such as by recombinant nucleic acid techniques and by synthetic nucleic acid synthesis or in vitro enzymatic synthesis.

The invention also provides for the isolated nucleic acid of SEQ ID NO:1 in a vector suitable for expressing the nucleic acid. Once a nucleic acid encoding a GP64-6 His protein of interest, or a region of that nucleic acid, is constructed, modified, or isolated, that nucleic acid can then be cloned into an appropriate vector, which can direct the in vivo or in vitro synthesis of that wild-type and/or modified GP64-6His protein. The vector is contemplated to have the necessary functional elements that direct and regulate transcription of the inserted gene, or nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al.).

There are numerous *E. coli* (*Escherichia coli*) expression vectors known to one of ordinary skill in the art which are useful for the expression of the nucleic acid insert. Other microbial hosts suitable for use include bacilli, such as *Bacillus subtilis*, and other enterobacteriaceae, such as *Salmonella, Serratia*, and various *Pseudomonas* species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MF"-1 gene) is routinely used to direct protein secretion from yeast. (Brake, et al., A %-Factor-Directed Synthesis and Secretion of Mature Foreign Proteins in *Saccharomyces cerevisiae*. Proc. Nat. Acad. Sci., 81:4642-4646 (1984)). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The nucleic acid coding sequence can be fused in-frame to the pre-pro-alpha-factor leader region. This construct is then put under the control of a strong transcription promoter, such as the alcohol dehydrogenase I promoter or a glycolytic promoter. The nucleic acid coding sequence is followed by a translation termination codon which is followed by transcription termination signals. Alternatively, the nucleic acid coding sequences can be fused to a second protein coding sequence, such as Sj26 or beta-galactosidase, used to facilitate purification of the fusion protein by affinity chromatography. The insertion of protease cleavage sites to separate the components of the fusion protein is applicable to constructs used for expression in yeast. Efficient post translational glycosylation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral promoter and a polyadenylation signal. The vectors can contain genes conferring hygromycin resistance, gentamicin resistance, or other genes or phenotypes suitable for use as selectable markers, or methotrexate resistance for gene amplification. The chimeric protein coding sequence can be introduced into a Chinese hamster ovary (CHO) cell line using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, or lipofectin mediated transfection or electroporation may be used for other cellular hosts.

Alternative vectors for the expression of genes or nucleic acids in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acids in mammalian cells (such as COS-7).

Insect cells also permit the expression of mammalian proteins. Recombinant proteins produced in insect cells with baculovirus vectors undergo post-translational modifications similar to that of wild-type proteins. Briefly, baculovirus vectors useful for the expression of active proteins in insect cells are characterized by insertion of the protein coding sequence downstream of the *Autographica californica* nuclear polyhedrosis virus (AcNPV) promoter for the gene encoding polyhedrin, the major occlusion protein. Cultured insect cells such as *Spodoptera frugiperda* cell lines are transfected with a mixture of viral and plasmid DNAs and the viral progeny are plated. Deletion or insertional inactivation of the polyhedrin gene results in the production of occlusion negative viruses which form plaques that are distinctively different from those of wild-type occlusion positive viruses. These distinctive plaque morphologies allow visual screening for recombinant viruses in which the AcNPV gene has been replaced with a hybrid gene of choice. High quantity expression and production of the GP64-6His protein can also be achieved by transgenic animal technology by which animals can be made to produce GP64-6His in serum, milk, etc in large amounts.

The invention also provides for the vectors containing the contemplated nucleic acids in a host suitable for expressing the nucleic acids. The vectors containing the nucleic acid segments of interest can be transferred into host cells by well-known methods, which vary depending on the type of cellular host. For example, calcium chloride transformation, transduction, and electroporation are commonly utilized for prokaryotic cells, whereas calcium phosphate, DEAE dextran, or lipofection mediated transfection or electroporation may be used for other cellular hosts.

Alternatively, the nucleic acid of the present invention can be operatively linked to one or more of the functional elements that direct and regulate transcription of the inserted gene as discussed above and the gene or nucleic acid can be expressed. For example, a nucleic acid can be operatively linked to a bacterial or phage promoter and used to direct the transcription of the gene or nucleic acid in vitro. A further example includes using a nucleic acid provided herein in a coupled transcription-translation system where the gene directs transcription and the RNA thereby produced is used as a template for translation to produce a polypeptide. One skilled in the art will appreciate that the products of these reactions can be used in many applications such as using labeled RNAs as probes and using polypeptides to generate antibodies or in a procedure where the polypeptides are being administered to a cell or a subject.

Expression of the nucleic acid, in combination with a vector, can be either in vivo or in vitro. In vivo synthesis comprises transforming prokaryotic or eukaryotic cells that can serve as host cells for the vector. Alternatively, expression of the nucleic acid can occur in an in vitro expression system. For example, in vitro transcription systems are commercially available which are routinely used to synthesize relatively large amounts of mRNA. In such in vitro transcription systems, the nucleic acid encoding the GP64-6His protein would be cloned into an expression vector adjacent to a transcription promoter. For example, the Bluescript II cloning and expression vectors contain multiple cloning sites which are flanked by strong prokaryotic transcription promoters. (Stratagene Cloning Systems, La Jolla, Calif.). Kits are available which contain all the necessary reagents for in vitro synthesis of an RNA from a DNA template such as the Bluescript vectors. (Stratagene Cloning Systems, La Jolla, Calif.). RNA produced in vitro by a system such as this can then be translated in vitro to produce the desired GP64-6His protein. (Stratagene Cloning Systems, La Jolla, Calif.).

In another aspect, the invention provides the polypeptides encoded by the nucleic acids set forth in SEQ ID NO:1 as well as the polypeptide set forth in the Sequence Listing as SEQ ID NO:2. This invention also provides GP64-His polypeptides that comprise histidine tags that contain at least five histidine residues. GP64-His proteins comprising a histidine tag that contains between 5 and 20 histidine residues are also provided. For example, a GP64-His polypeptide of this invention can comprise a histidine tag containing 5, 6, 7, 8, 9, 10, 11, 12, 13, 14, 15, 16, 17, 18, 19 or 20 histidine residues.

The invention also provides fragments of unmodified and modified GP64-6His polypeptides. For example, a fragment of a GP64-6His polypeptide can be a chimeric GP64-6His polypeptide that comprises GP64-6His and a fragment of a polypeptide of interest. Another example is a fragment of a GP64-6His polypeptide that comprises a fragment of GP64 linked to 6His. The polypeptide fragments of the present invention can be recombinant proteins obtained by cloning nucleic acids encoding the polypeptide in an expression system capable of producing the polypeptide fragments thereof. For example, one skilled in the art can determine the active regions of a GP64-6His protein which can interact with another protein, lipid or other molecule and cause a biological effect associated with the GP64-6His protein. In one example, amino acids found to not contribute to either the activity, binding specificity, or other biological effect associated with the GP64-6His protein can be deleted and/or substituted without a loss in the respective activity. The fragments, whether attached to other sequences or not, can also include insertions, deletions, substitutions, or other selected modifications of particular regions or specific amino acid residues, provided the activity of the peptide is not significantly altered or impaired. Further contemplated are polypeptides encoded by fragments of the GP64-6His nucleic acids provided herein.

Further provided by this invention is a GP64-6His polypeptide further comprising a binding site for a cell surface molecule. As described above, there are several methods for obtaining the GP64-6His polypeptides of this invention. The binding site can be a protein, a peptide, a ligand, a carbohydrate moiety, viral proteins, a monoclonal antibody or a polyclonal antibody. This binding site allows targeting of a GP64-6His polypeptide to a particular cell type. For example, a ligand or a portion of a ligand that binds to a cell surface receptor can be attached to the GP64-6His polypeptide to target the GP64-6His polypeptide to a cell surface receptor on specific cells. These GP64-6His polypeptides containing a binding site can be utilized to target a polypeptide that is conjugated to a GP64-6His polypeptide to a specific cell type. It can also be reconstituted into a liposome comprising a biological molecule, DNA vaccine or viral vaccine such that when the liposoine comprising this GP64-6His is administered, the contents of the liposome can be delivered to a specific cell type. By "attached" is meant that the binding site can be conjugated to the ends of the GP64-6His polypeptide or the binding site may be incorporated into a region of the GP64-6His polypeptide.

The binding site can also be used to purify GP64-6His by immobilizing a molecule that interacts with the binding site on a column and allowing the GP64-6His to bind to the column. One skilled in the art would know the appropriate conditions for releasing the peptide from the column subsequent to binding.

The GP64-6His polypeptides of this invention also include chimeric polypeptides comprising GP64-6His wherein another protein or a peptide is linked or chemically conjugated to GP64-6His to make a chimeric protein. The protein or peptide linked to GP64-6His can be delivered to cells via the GP64-6His fusion mechanism. Once GP64-6His mediates fusion, the protein or peptide linked to GP64-6His is delivered to a cell. There a methods known to own skilled in the art for linking a protein or peptide to GP64-6His such that, once inside the cell, the chimeric protein is cleaved or reduced to remove GP64-6His.

These GP64-6His polypeptides can also be obtained in any of a number of procedures well known in the art. One method of producing a polypeptide is to link two peptides or polypeptides together by protein chemistry techniques. For example, peptides or polypeptides can be chemically synthesized using currently available laboratory equipment using either Fmoc (9-fluorenylmethyloxycarbonyl) or Boc (tert -butyloxycarbonoyl) chemistry. (Applied Biosystems, Inc., Foster City, Calif.). One skilled in the art can readily appreciate that a peptide or polypeptide corresponding to a particular protein can be synthesized by standard chemical reactions. For example, a peptide or polypeptide can be synthesized and not cleaved from its synthesis resin whereas the other fragment of a hybrid peptide can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a larger polypeptide. (Grant, Synthetic Peptides: A User Guide, W. H. Freeman and Co., N.Y. (1992) and Bodansky and Trost, Ed., Principles of Peptide Synthesis, Springer-Verlag Inc., N.Y. (1993)). Alternatively, the peptide or polypeptide can be independently synthesized in vivo as described above. Once isolated, these independent peptides or polypeptides may be linked to form a larger protein via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al. Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. A Synthesis of Proteins by Native Chemical Ligation, Science, 266:776-779 (1994)). The first step is the chemoselective reaction of an unprotected synthetic peptide-∞-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Clark-Lewis et al. FEBS Lett., 307:97 (1987), Clark-Lewis et al., J. Biol. Chem., 269:16075 (1994), Clark-Lewis et al. Biochemistry, 30:3128 (1991), and Rajarathnam et al. Biochemistry, 29:1689 (1994)).

Alternatively, unprotected peptide segments can be chemically linked where the bond formed between the peptide segments as a result of the chemical ligation is an unnatural (non-peptide) bond (Schnolzer et al Science, 256:221 (1992)). This technique has been used to synthesize analogs of protein domains as well as large amounts of relatively pure proteins with full biological activity (deLisle Milton et al. Techniques in Protein Chemistry IV, Academic Press, New York, pp. 257-267 (1992)).

Also provided herein are purified antibodies that selectively or specifically bind to the GP64-6His polypeptides provided and contemplated herein, for example, purified antibodies which selectively or specifically bind to the polypeptide or polypeptide fragments encoded by the nucleic acid set forth in any of SEQ ID NO:1, and purified antibodies which selectively or specifically bind to the polypeptide set forth in SEQ ID NO:2 or fragments thereof. The antibody (either polyclonal or monoclonal) can be raised to any of the polypeptides provided and contemplated herein, both naturally occurring and recombinant polypeptides, and immunogenic fragments, thereof. Anti-idiotypic antibodies and affinity matured antibodies are also considered.

Antibodies can be made by many well-known methods (See, e.g. Harlow and Lane, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al. *Bio/Technology*, 10:163-167 (1992); Bebbington et al. *Bio/Technology*, 10:169-175 (1992)). Humanized and chimeric antibodies are also contemplated in this invention. Heterologous antibodies can be made by well known methods (See, for example, U.S. Pat. Nos. 5,545,806, 5,569,825, 5,625,126, 5,633,425, 5,661,016, 5,770,429, 5,789,650, and 5,814,318).

The phrase "specifically binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York, (1988), for a description of immunoassay formats and conditions that could be used to determine selective binding.

The invention further provides a liposome comprising a GP64-6His polypeptide of this invention. For example, a liposome can comprise a GP64-6His polypeptide encoded by SEQ ID NO: 1 or the polypeptide set forth in SEQ ID NO: 2. The liposomes of this invention can comprise cationic, anionic and zwitterionic components. In essence, the liposome of this invention can be positively charged, negatively charged or neutral. For example, cationic components include, but are not limited to DOTMA and PC/cholesterol. An example of a zwitterionic component is DOPE. The composition of the liposomes may vary as well. For example, the liposome may include sphingomyelin, cholesterol or a ganglioside such as $G_{M1}$, among others, depending on the degree of liposomal stabilization desired (Hug and Sleight, "Liposomes for the transformation of eukaryotic cells," Biochimica et. Biophysica Acta 1097:1-17 (1991)). The liposome can also comprise a targeting moiety such as a protein, a peptide, a ligand, a carbohydrate moiety, viral proteins, a monoclonal antibody or a polyclonal antibody that targets the liposome comprising a GP64-6His polypeptide to a specific cell type. These targeting moieties can be covalently attached to the outside of existing liposomes or integrated into the membrane as the liposome is formed. Liposomes comprising GP64-6His in combination with a nuclear localization signal peptide for delivery to the nucleus can be utilized as well.

The liposome of this invention can also comprise an antigen that stimulates the immune system to provide an immune response. The antigen can be any substance or molecule, such as a chemical, a protein, a polypeptide, a bacteria, a virus, a bacterial protein or fragment thereof, a viral protein or fragment thereof or any other molecule that elicits an immune response.

A liposome comprising a GP64-6His polypeptide of this invention can further comprise a biological molecule such as sense or antisense nucleic acids (e.g. DNA, RNA), a protein, a toxin or a drug. A method of preparing liposomes comprising a GP64-6His polypeptide as well as a method of preparing liposomes comprising a GP64-6His polypeptide and a biological molecule are provided in the Examples. Similarly, a GP64-6His chimeric polypeptide or a GP64-6His polypeptide comprising a binding site can be incorporated into liposomes. The liposome comprising a GP64-6His polypeptide can further comprise a vaccine, such as a DNA vaccine or a viral vaccine. GP64-6His liposomes encapsulating drugs or antisense RNA should protect them from destruction by the lysosome and facilitate intracellular release of the liposome payload.

Also provided by this invention is a liposome that comprises a GP64-6His polypeptide that further comprises a binding site for a cell surface molecule. Further provided is a liposome that comprises a GP64-6His polypeptide that further comprises a binding site for a cell surface molecule, wherein the binding site recognizes a cell surface molecule on a specific cell type. The liposomes can further comprise a biological molecule, a DNA vaccine or a viral vaccine.

The invention further provides a method of delivering a biological molecule to a cell comprising administering the liposome comprising GP64-6His and a biological molecule to a cell whereby the GP64-6His mediates membrane fusion, thus delivering the biological molecule to the cell.

Also contemplated by this invention is a method of delivering a DNA vaccine to a cell comprising: administering the liposome comprising GP64-6His and a DNA vaccine to a cell whereby the GP64-6His mediates membrane fusion thus delivering the DNA vaccine to the cell.

High levels of humoral and cell-mediated immunity can be achieved via administration of DNA vaccines. Numerous studies have shown that immunization of experimental animals with plasmid DNA encoding antigens from a wide spectrum of bacteria, viruses, protozoa and cancers leads to protective humoral and cell-mediated immunity (Gregoriadis G. "Genetic vaccines: strategies for optimization" Pharm Res. 15:661-70 (1998)).

Liposomes have been widely used to enhance the immune response. For example, a DNA vaccine constructed with the CMV promoter conjugated to env gp160 and rev genes has been shown to induce an effective immune response when inoculated via intramuscular, intraperitoneal, subcutaneous, intradermal and intranasal routes (Fukushima I. N. "Cationic liposomes are a strong adjuvant for a DNA vaccine of human immunodeficiency virus type 1" 13:1421-1428 (1997)). By immunizing with pCMV160/REV and cationic liposomes through various routes higher levels of both antibody production and delayed-type hypersensitivity were induced than by using DNA vaccine alone.

DNA vaccines can also be administered in combination with other agents in liposomes to increase levels of immunity. Coadministration of the DNA vaccine with IL-12 and granulocyte/macrophage CSF-expressing plasmids induced high levels of HIV-specific circulating T lymphocytes and in increase in delayed type hypersensitivity when administered by the intranasal route. The results indicate that intranasal administration of this DNA vaccine with liposomes, together with IL-12 and/or granulocyte/macrophage-CSF expressing plasmids, induces a strong level of anti-HIV-1 immune response (Okada E. "Intranasal immunization of a DNA vaccine with IL-12 and granuloctye-macrophage colony-stimulating factor (GM-CSF)-expressing plasmids in liposomes induces strong mucosal and cell-mediated immune responses against HIV-1 antigens" 159:3638-47 (1997)).

The invention also provides a method of delivering a viral vaccine to a cell comprising, administering a liposome comprising GP64-6His and a viral vaccine to a cell whereby the GP64-6His mediates membrane fusion thus delivering the viral vaccine to the cell.

In a viral vaccine, viral particles or peptides derived from viruses can be attached or incorporated into liposomes to induce immunity. For example, inactivated hepatitis A virus particles were attached to phospholipid vesicles together with influenza virus haemmuglutinin and were administered to volunteers. This vaccine was tolerable and highly immunogenic resulting in long lasting immunity (Ambrosch F. "Immunogenicity and protectivity of a new liposomal hepatitis A vaccine" Vaccine 15:1209-13 (1997)). Similarly, a peptide derived from influenza virus A/Aichi/2/68(H3N2) that was loaded in multilamellar liposomes without adjuvant protects the mice against infection with Aichi/68 within 2 weeks after final immunization. Further, this viral vaccine was shown to be effective in preventing infection with a naturally occurring antigenic variant, A/Texas/1/77(H3N2), carrying the same sequence at 127-133 of the HA as Aichi/68 virus (Naruse H. "A potential peptide vaccine against two different strains of influenza virus isolated at intervals of about 10 years" PNAS 91:9588-92 (1994)).

Since GP64-6His liposomes can potentially deliver antigenic proteins intact to the cellular interior. This should ultimately result in the breakdown of these proteins and presentation of peptide fragments via MHC class I on the cell surface. The net result of this should be stimulation of a strong cellular (Cytotoxic T cell) response. An additional advantage would be that liposomes containing protein antigen are highly stimulating to the antibody response due presumably to the high local concentration of antigen. Lastly there is some immunologic work to suggest that massive doses of antigen can induce immunologic tolerance. It may be possible to use this system to deliver large quantities of antigen in vivo, which could induce tolerance to specific antigens. Therefore, GP64-6His liposomes may provide a means of delivery of locally high concentrations of antigen(s) to critical tissues or cells which regulate immune responses. Potential applications of this include 1) reduction or elimination of allergic responses, 2) treatment of auto immune responses, perhaps permitting the body to cease responding to attacking itself and 3) blocking or inhibiting immune responses against transplanted organs.

The liposome comprising GP64-6His and a biological molecule, DNA vaccine or viral vaccine can be delivered to a specific cell type by covalently attaching a targeting moiety to a liposome or allowing the targeting moiety to become integrated into the membrane as the liposome is formed. The targeting moiety can bind to a specific cell type allowing GP64 to mediate membrane fusion, thus allowing the contents of the liposome to be delivered to a cell. For example, a targeting moiety specific for tumor cells can be incorporated into the liposome comprising GP64 and a toxin. Upon delivery of the liposome, the targeting moiety will bind to a tumor cell allowing GP64 to mediate membrane fusion, thus allowing the toxin to enter the tumor cell. Alternatively, the targeting moiety can be a ligand that binds to a cell surface protein or receptor. Numerous cell-specific cell surface proteins are known which can be targeted by the present invention by incorporating a ligand for the cell surface protein into the liposomes of the present invention.

Similarly, an antibody can be incorporated into the liposome comprising GP64-6His that will target a specific antigen on a cell. Upon delivery, the antibody will bind to the antigen on a specific cell type and GP64 will mediate membrane fusion thus allowing the contents of the liposome to be delivered to the cell.

With respect to targeting GP64-6His to specific cell types, it is well known that glycoproteins expressed in Sf9 cells lack terminal sialic acid residues (neuraminic acid) (Hollister et al. "GP64 does not contain sialic acid when synthesized in insect cells" *Glycobiology,* 8:473-480 (1998); Jarvis and Garcia "Biosynthesis and processing of the *autographa californica* nuclear polyhedrosis virus gp64 protein" *Virology* 205:300-313 (1994)). This altered glycosylation pattern should make GP64 liposomes a target for the asialoglycoprotein receptor of the liver. Consequently GP64 liposomes may specifically target the liver when injected into the blood stream.

This invention also provides a method of delivering a biological molecule to a specific cell type comprising: administering the liposome that comprises a GP64-6His polypeptide that further comprises a binding site for a cell surface molecule to a cell whereby the GP64-6His mediates membrane fusion, thus delivering the biological molecule to a specific cell type. Numerous cell-specific cell surface proteins are known which can be targeted by the present invention by combining a ligand for that protein with the GP64-6His of the present invention. For example, a GP64-6His polypeptide can comprise a binding site that is recognized by a specific integrin receptor. Similarly, a GP64-6His polypeptide can comprise a hormone or hormone fragment that is recognized by a particular hormone receptor.

A method of delivering a viral vaccine to a specific cell type comprising: administering the liposome that comprises a GP64-6His polypeptide that further comprises a binding site for a cell surface molecule to a cell whereby the GP64-6His mediates membrane fusion, thus delivering the viral vaccine to a specific cell type.

Also provided by this invention is a method of delivering a DNA vaccine to a specific cell type comprising: administering the liposome that comprises a GP64-6His polypeptide that further comprises a binding site for a cell surface molecule to a cell whereby the GP64-6His mediates membrane fusion, thus delivering the DNA vaccine to a specific cell type.

In the methods described above, the liposomes of this invention, can be in a pharmaceutically acceptable carrier for in vivo administration to a subject. By "pharmaceutically acceptable" is meant a material that is not biologically or otherwise undesirable, i.e., the material may be administered to a subject, along with the nucleic acid or vehicle, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

A liposome comprising GP64-6His may be delivered or administered orally, parenterally (e.g., intravenously), by intramuscular injection, by intraperitoneal injection, intratracheally, transdermally, extracorporeally, intranasally, topically or the like. With respect to oral administration, GP64 rapidly mediates membrane fusion when exposed to acidic pH. GP64-mediated fusion can occur at a $t_{1/2}$ of less than 0.5 seconds. This feature may potentially allow liposome encapsulated materials (drugs, nucleic acids, proteins, hormones etc) to be ingested orally and absorbed by cells lining the digestive tract as the GP64 containing liposomes come into contact with the acidic GI tract.

The exact amount of the liposome comprising GP64-6His required will vary from subject to subject, depending on the species, age, weight and general condition of the subject, the severity or mechanism of any disorder being treated, the particular liposome used, its mode of administration and the like.

The subject of these methods can be any animal. In a preferred embodiment, the animal of the present invention is a human. In addition, non-human animals which can be treated by the methods of this invention can include, but are not limited to, cats, dogs, birds, horses, cows, goats, sheep, guinea pigs, hamsters, gerbils and rabbits.

As mentioned above, the contents of the liposome can be DNA which once introduced into the cytoplasm of a cell, can enter the nucleus and express the gene of interest. Transfer of nucleic acids or genes can be accomplished in vitro or ill vivo. Liposomal delivery of DNA has resulted in stable gene transfer and expression in mice. Subcutaneous injection of liposomes containing a plasmid expressing the early region of polyoma virus resulted in expression of polyoma virus early proteins in 50% of the mice in the experimental group (Gould-Fogerite et al. "Chimerasome-mediated gene transfer in vitro and in vivo" Gene, 84:429-438 (1989)).

Being relatively large, a liposome could deliver essentially any combination of types and amount of genetic material. Liposomes known as stealth or PEG liposomes have recently been developed which reduce or prevent immune responses against circulating liposomes (Vertut-Doi et al. "Binding and uptake of liposomes containing a poly(ethylene glycol) derivative of cholesterol (stealth liposomes) by the macrophage cell line J774: influence of PEG content and its molecular weight" *Biochim Biophys Acta* 1278:19-28 (1996); Kedar et al. "Delivery of cytokines by liposomes. II. Interleukin-2 encapsulated in long-circulating sterically stabilized liposomes: immunomodulatory and anti-tumor activity in mice" *J. Immunotherp. Emphasis Tumor Immunol.* 16: 115-124 (1994); Working et al. "Reduction of the cardiotoxicity of doxorubicin in rabbits and dogs by encapsulation in long-circulating, pegylated liposomes" *J. Pharmacol. Exp Ther.* 289: 1128-33 (1999); Vaage et al. "Therapy of a xenografted human colonic carcinoma using cisplatin or doxorubicin encapsulated in long-circulating pegylated stealth liposomes" *Int. J. Cancer* 80: 134-137 (1999). This technology is applicable to GP64-6His liposomes. Since the size or amount of DNA is not restricted, it is possible to utilize homologous recombination strategies such as those used for knock-out mouse technology to directly target the gene of interest.

This invention further provides a method of increasing the solubility of polypeptides comprising linking a 6His tag to a polypeptide and measuring the solubility of the 6His-tagged polypeptide, whereby an increase in solubility of the 6His-tagged polypeptide can be detected. Depending on the charge associated with a particular polypeptide, the polypeptide's solubility can be increased by altering the number of histidines necessary to increase its solubility. Therefore, the solubility of a particular polypeptide can be increased by adding a tag comprising 5, 6, 7, 8, 9, 10, 11, 12, 13, 14, 15, 16, 17, 18, 19 or 20 histidine residues.

Solubility can be assessed as described in the Examples. Briefly, cells containing a 6His-tagged polypeptide can be lysed with detergents, followed by binding of the 6His-tagged polypeptide to a nickel column. The column is then washed several times and the 6His-tagged polypeptide is eluted. The polypeptide is then concentrated by centrifugation. If the polypeptide does not remain soluble, this centrifugation would result in insoluble pellet formation. If the polypeptide remains soluble, SDS-PAGE analysis can be utilized to confirm that the polypeptide remained in the liquid concentrate. If a polypeptide that is normally insoluble, i.e. appears in an insoluble pellet upon low speed centrifugation is found to be soluble upon addition of a 6His tag, i.e. appears in the liquid concentrate after centrifugation, an increase in solubility has occurred.

The invention also provides a method of solubilizing a viral fusion polypeptide comprising linking a 6His tag to a viral fusion polypeptide such as GP64. A method for constructing a GP64-6His polypeptide is described above and in the Examples.

The present invention is more particularly described in the following examples which are intended as illustrative only since numerous modifications and variations therein will be apparent to those skilled in the art.

EXAMPLES

Construction and Expression of GP64-6His

Sf9 cell expression plasmid, ATH-1, was obtained from Gary Blissard at Cornell Univ. To create the GP64-6His expression vector, a BclI site was created by mutagenesis at nt 1753 of the ATH-1 sequence and an oligonucleotide cassette (5' GAT CAG AAA CCG TAA TAG AGA ATA T CAT CAC CAT CAC CAT CAC TAG 3' (SEQ ID NO: 3) and 5' CTA GTG ATG GTG ATG GTG ATG A TAT TCT CTA TTA CGG TTT CT 3' (SEQ ID NO: 4)), encoding 6 histidines was inserted. This construct then expressed the complete and exact GP64 amino acid sequence with the cytoplasmic tail extended by six histidines. Sf9 cells were obtained from the American Type Culture Collection (Manassas, Va.) and cultured at 28° C. in Grace's insect cell media (Invitrogen, Carlsbad Calif.) supplemented with 10% fetal bovine serum and 50 units/ml penicillin and 50 mg/ml streptomycin. Cells used were only used until their 25th passage. To test fusion function GP64-6His was expressed on the surface of Sf9 cells using $Ca_3(PO_4)_2$ transfection. 48 hrs posttransfection growth media was removed and syncytia formation was triggered by addition of PBS pH 5.0.

Purification of GP64-6His

SF9 cells were transfected with GP64-6His plasmid (80-90% confluent) with plasmid. Typically 50-200 µg plasmid were added per t75 flask. Transfected SF9 cells were cultured for 48-72 hrs. Media was removed and replaced with 5 mls PBS. Cells were detached from the flask using a cell scraper. Cells were centrifuged at 1000 rpm in a Beckman J6-M centrifuge for 5 min. Cells were resuspended in Cold PBS and the process was repeated twice. Cells were lysed in Lysis buffer using 1 ml per transfected T75 flask. [Lysis buffer=1% triton, 1×PBS without Ca/Mg, 20 mM Imidizole, and AEBSF protein inhibitors (0.1 mM)]. Lysate was clarified by centrifugation at 3000 rpm in the J6-M 5 min. Supernatant was loaded on column containing 70 µl nickel resin (Ni-NTA Agarose, QiagenCorp, Valencia Calif.) per T75 flask (normally 700 µl).

The column was washed in solution #2 (150 mM NaCl, 1×PBS (no Ca/Mg), 20 mM Imidizole, 1% triton, 0.1 mM AEBSF). Typically 1 ml. The column was successively washed with 1×PBS w/o, 0.1 mM AEBSF, 60 mM Imidizole and then the same solution with 80 mM Imidizole. Protein was eluted with 1×PBS w/o, 0.1 mM AEBSF 250 mM Imidizole. Elute from the column was concentrated and purity was estimated to be in excess of 90% by SDS-PAGE. Enzyme-linked immunosorbant assay using the AcV1 antibody which recognizes a discontinous epitope found only in the neutral pH conformation of GP64 indicates that purified GP64-6His has some native structure.

In order to assess solubility, cells were lysed with detergents, GP64-6His was bound to a nickel column, eluted and centrifuged as described above. After concentrating the protein by centrifugation, if the protein had not remained soluble this centrifugation would have resulted in insoluble pellet formation. SDS-PAGE analysis of the concentrate indicated that the protein remained in the liquid concentrate (supernatant).

Procedures for Creation of GP64-6His Containing Proteoliposomes

GP64-6His containing liposomes were made from a 1 mM lipid mixture as follows 5% PE-Rhodamine or 5% (1,2 dioleoyl-sn-Glycerol-3-phosphoethanolamine-N-Lissamine Rhodamine B sulfonyl Cat # 810150 Avanti polar), or 5% Dioleyl phosphoethanolamine (DOPE), 47.5% palmytic oleic phosphocholine (POPC), 47.5% cholesterol. Fluorescent liposomes contain PE-Rhodamine. Nonfluorescent liposomes were made using 5% DOPE. A 10× lipid stock was made of Rh-PE, or DOPE, POPC, Cholesterol in Benzene/MeoH(95:5) were mixed dried under vacuum for 1 hr. Dried lipids were resuspended in 100 µl Triton X-100 (Sigma Corp, St Louis, Mo.) and 900 ul PBS. One hundred microliters of 10× stock with 10-100 µg GP64-6His-and up to 900 ul PBS without Ca/Mg. Approximately 500 µl Add Biobeads (SM-2 Biorad Inc, Richmond Calif.)-pretreated with 100% MeOH and 3× with PBS). extract 4 hrs-O/N at 4C. Add a second batch of Biobeads extract again 4 hrs+. Liposomes created in this manner have been sized by a particle sizer (Model N4 Plus, Coulter Corp, Miami Fla.). Flourescent dequenching of liposomes was assessed using a Lumenescence Spectrometer (Amico-Bowman Inc.).

Evaluation of Fusion by GP64-6His Containing Liposomes

When rhodamine containing liposomes with and without GP64-6His have been added to Sf9 cell cultures followed by low pH buffer application, a greater degree and more diffuse pattern of fluorescence has been observed by microscopic examination for liposomes with GP64-6His compared to those without.

Throughout this application, various publications are referenced. The disclosures of these publications in their entireties are hereby incorporated by reference into this application in order to more fully describe the state of the art to which this invention pertains.

What is claimed is:

1. A liposome comprising the GP64-6His polypeptide encoded by the nucleic acid set forth in the Sequence Listing as SEQ ID NO: 1, wherein said GP64-6His polypeptide is exposed to the exterior environment, and further comprising a virus vaccine.

2. A liposome comprising the GP64-6His polypeptide encoded by the nucleic acid set forth in the Sequence Listing as SEQ ID NO: 1, wherein said GP64-6His polypeptide is exposed to the exterior environment, and further comprising a DNA vaccine.

3. A method of delivering a viral vaccine to a cell comprising administering to a cell a liposome comprising the GP64-6His polypeptide encoded by the nucleic acid set forth in the Sequence Listing as SEQ ID NO: 1, wherein said GP64-6His polypeptide is exposed to the exterior environment, and further comprising a virus vaccine.

4. A method of delivering a DNA vaccine to a cell comprising administering to a cell a liposome comprising the GP64-6His polypeptide encoded by the nucleic acid set forth in the Sequence Listing as SEQ ID NO: 1, wherein said GP64-6His polypeptide is exposed to the exterior environment, and further comprising a DNA vaccine.

5. A liposome comprising a GP64-6His polypeptide comprising a binding site for a cell surface molecule, wherein said GP64-6His polypeptide is encoded by the nucleic acid set forth in the Sequence Listing as SEQ ID NO: 1 and is exposed to the exterior environment.

6. The liposome of claim 5, wherein the binding site recognizes a cell surface molecule on a specific cell type.

7. The liposome of claim 6, further comprising a biological molecule.

8. The liposome of claim 6, further comprising a viral vaccine.

9. The liposome of claim 6, further comprising a DNA vaccine.

10. A method of delivering biological molecule to a specific cell type comprising: administering the liposome of claim 7 to a cell.

11. A method of delivering a viral vaccine to a specific cell type comprising: administering the liposome of claim 8 to a cell.

12. A method of delivering a DNA vaccine to a specific cell type comprising: administering the lipo some of claim 9 to a cell.

* * * * *

UNITED STATES PATENT AND TRADEMARK OFFICE
CERTIFICATE OF CORRECTION

PATENT NO. : 7,662,619 B2 Page 1 of 1
APPLICATION NO. : 10/416979
DATED : February 16, 2010
INVENTOR(S) : Kingsley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1452 days.

Signed and Sealed this

Thirtieth Day of November, 2010

David J. Kappos
*Director of the United States Patent and Trademark Office*

SEQUENCE LISTING

```
<160> NUMBER OF SEQ ID NOS: 4

<210> SEQ ID NO 1
<211> LENGTH: 1554
<212> TYPE: DNA
<213> ORGANISM: Artificial Sequence
<220> FEATURE:
<223> OTHER INFORMATION: Description of Artificial Sequence.
      Note/Artificial Sequence = synthetic construct

<400> SEQUENCE: 1
atggtaagcg ctattgtttt atatgtgctt ttggcggcgg cggcgcattc tgcctttgcg      60
gcggagcact gcaacgcgca aatgaagacg ggtccgtaca agattaaaaa cttggacatt     120
accccgccca aggaaacgct gcaaaaggac gtggaaatca ccatcgtgga gacggactac     180
aacgaaaacg tgattatcgg ctacaagggg tactaccagg cgtatgcgta caacggcggc     240
tcgctggatc ccaacacacg cgtcgaagaa accatgaaaa cgctgaatgt gggcaaagag     300
gatttgctta tgtggagcat caggcagcag tgcgaggtgg gcgaagagct gatcgaccgt     360
```

```
tggggcagtg acagcgacga ctgttttcgc gacaacgagg gccgcggcca gtgggtcaaa    420
ggcaaagagt tggtgaagcg gcagaataac aatcactttg cgcaccacac gtgcaacaaa    480
tcgtggcgat gcggcatttc cacttcgaaa atgtacagca ggctcgagtg ccaggacgac    540
acggacgagt gccaggtata cattttggac gctgagggca cccccatcaa cgtgaccgtg    600
gacactgtgc ttcatcgaga cggcgtgagt atgattctca aacaaaagtc tacgttcacc    660
acgcgccaaa taaagctgc gtgtctgctc attaaagatg acaaaaataa ccccgagtcg    720
gtgacacgcg aacactgttt gattgacaat gatatatatg atctttctaa aaacacgtgg    780
aactgcaagt ttaacagatg cattaaacgc aaagtcgagc accgagtcaa gaagcggccg    840
cccacttggc gccacaacgt tagagccaag tacacagagg gagacactgc caccaaaggc    900
gacctgatgc atattcaaga ggagctgatg tacgaaaacg atttgctgaa atgaacatt    960
gagctgatgc atgcgcacat caacaagcta acaatatgc tgcacgacct gatagtctcc   1020
gtggccaagg tggacgagcg tttgattggc aatctcatga caactctgt ttcttcaaca   1080
ttttttgtcgg acgacacgtt tttgctgatg ccgtgcacca atccgccggc acacaccagt   1140
aattgctaca caacagcat ctacaaagaa gggcgttggg tggccaacac ggactcgtcg   1200
caatgcatag attttcgcaa ctacaaggaa cttgcaattc acgacgtcga gttttggatc   1260
ccgaccatcg gcaacacgac ctatcacgac agttggaaag atgccagcgg ctggtcgttt   1320
attgcccaac aaaaaagcaa cctcataacc accatggaga acaccaagtt tggcggcgtc   1380
ggcaccagtc tgagcgacat cacttccatg gctgaaggcg aattggccgc taaattgact   1440
tcgttcatgt ttggtcatgt agttaacttt gtaattatat taattgtgat tttatttttg   1500
tactgtatga tcagaaaccg taatagacaa tatcatcacc atcaccatca ctag         1554
```

<210> SEQ ID NO 2
<211> LENGTH: 517
<212> TYPE: PRT
<213> ORGANISM: Artificial Sequence
<220> FEATURE:
<223> OTHER INFORMATION: Description of Artificial Sequence.
      Note/Artificial Sequence = synthetic construct

<400> SEQUENCE: 2

```
Met Val Ser Ala Ile Val Leu Tyr Val Leu Leu Ala Ala Ala His
 1               5                  10                  15

Ser Ala Phe Ala Ala Glu His Cys Asn Ala Gln Met Lys Thr Gly Pro
            20                  25                  30

Tyr Lys Ile Lys Asn Leu Asp Ile Thr Pro Pro Lys Glu Thr Leu Gln
        35                  40                  45

Lys Asp Val Glu Ile Thr Ile Val Glu Thr Asp Tyr Asn Glu Asn Val
    50                  55                  60

Ile Ile Gly Tyr Lys Gly Tyr Tyr Gln Ala Tyr Ala Tyr Asn Gly Gly
65                  70                  75                  80

Ser Leu Asp Pro Asn Thr Arg Val Glu Glu Thr Met Lys Thr Leu Asn
                85                  90                  95

Val Gly Lys Glu Asp Leu Leu Met Trp Ser Ile Arg Gln Gln Cys Glu
            100                 105                 110

Val Gly Glu Glu Leu Ile Asp Arg Trp Gly Ser Asp Ser Asp Asp Cys
        115                 120                 125

Phe Arg Asp Asn Glu Gly Arg Gly Gln Trp Val Lys Gly Lys Glu Leu
    130                 135                 140
```

```
Val Lys Arg Gln Asn Asn Asn His Phe Ala His His Thr Cys Asn Lys
145                 150                 155                 160

Ser Trp Arg Cys Gly Ile Ser Thr Ser Lys Met Tyr Ser Arg Leu Glu
            165                 170                 175

Cys Gln Asp Asp Thr Asp Glu Cys Gln Val Tyr Ile Leu Asp Ala Glu
            180                 185                 190

Gly Asn Pro Ile Asn Val Thr Val Asp Thr Val Leu His Arg Asp Gly
            195                 200                 205

Val Ser Met Ile Leu Lys Gln Lys Ser Thr Phe Thr Thr Arg Gln Ile
        210                 215                 220

Lys Ala Ala Cys Leu Leu Ile Lys Asp Asp Lys Asn Asn Pro Glu Ser
225                 230                 235                 240

Val Thr Arg Glu His Cys Leu Ile Asp Asn Asp Ile Tyr Asp Leu Ser
                245                 250                 255

Lys Asn Thr Trp Asn Cys Lys Phe Asn Arg Cys Ile Lys Arg Lys Val
            260                 265                 270

Glu His Arg Val Lys Lys Arg Pro Pro Thr Trp Arg His Asn Val Arg
        275                 280                 285

Ala Lys Tyr Thr Glu Gly Asp Thr Ala Thr Lys Gly Asp Leu Met His
290                 295                 300

Ile Gln Glu Glu Leu Met Tyr Glu Asn Asp Leu Leu Lys Met Asn Ile
305                 310                 315                 320

Glu Leu Met His Ala His Ile Asn Lys Leu Asn Asn Met Leu His Asp
                325                 330                 335

Leu Ile Val Ser Val Ala Lys Val Asp Glu Arg Leu Ile Gly Asn Leu
            340                 345                 350

Met Asn Asn Ser Val Ser Ser Thr Phe Leu Ser Asp Asp Thr Phe Leu
        355                 360                 365

Leu Met Pro Cys Thr Asn Pro Pro Ala His Thr Ser Asn Cys Tyr Asn
370                 375                 380

Asn Ser Ile Tyr Lys Glu Gly Arg Trp Val Ala Asn Thr Asp Ser Ser
385                 390                 395                 400

Gln Cys Ile Asp Phe Arg Asn Tyr Lys Glu Leu Ala Ile His Asp Val
                405                 410                 415

Glu Phe Trp Ile Pro Thr Ile Gly Asn Thr Thr Tyr His Asp Ser Trp
            420                 425                 430

Lys Asp Ala Ser Gly Trp Ser Phe Ile Ala Gln Gln Lys Ser Asn Leu
        435                 440                 445

Ile Thr Thr Met Glu Asn Thr Lys Phe Gly Gly Val Gly Thr Ser Leu
450                 455                 460

Ser Asp Ile Thr Ser Met Ala Glu Gly Glu Leu Ala Ala Lys Leu Thr
465                 470                 475                 480

Ser Phe Met Phe Gly His Val Val Asn Phe Val Ile Ile Leu Ile Val
                485                 490                 495

Ile Leu Phe Leu Tyr Cys Met Ile Arg Asn Arg Asn Arg Gln Tyr His
            500                 505                 510

His His His His
        515

<210> SEQ ID NO 3
<211> LENGTH: 46
<212> TYPE: DNA
<213> ORGANISM: Artificial Sequence
```

-continued

```
<220> FEATURE:
<223> OTHER INFORMATION: Description of Artificial Sequence.
      Note/Artificial Sequence = synthetic construct

<400> SEQUENCE: 3
gatcagaaac cgtaatagag aatatcatca ccatcaccat cactag                46

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence.
      Note/Artificial Sequence = synthetic construct

<400> SEQUENCE: 4
ctagtgatgg tgatggtgat gatattctct attacggttt ct                    42
```